United States Patent [19]

Hoffman et al.

[11] 4,450,171

[45] * May 22, 1984

[54] ANTIHYPERCHOLESTEROLEMIC COMPOUNDS

[75] Inventors: William F. Hoffman; Robert L. Smith, both of Lansdale, Pa.; Alvin K. Willard, Wilmington, Del.

[73] Assignee: Merck & Co., Inc., Rahway, N.J.

[*] Notice: The portion of the term of this patent subsequent to Apr. 24, 2001 has been disclaimed.

[21] Appl. No.: 388,372

[22] Filed: Jun. 14, 1982

Related U.S. Application Data

[63] Continuation-in-part of Ser. No. 217,640, Dec. 18, 1980, which is a continuation-in-part of Ser. No. 175,460, Aug. 5, 1980, abandoned, which is a continuation-in-part of Ser. No. 118,051, Feb. 4, 1980, abandoned.

[51] Int. Cl.³ .................. C07C 69/74; A61K 31/335; C07D 309/30
[52] U.S. Cl. ................... 424/279; 549/292; 560/119; 560/256; 424/305; 424/311
[58] Field of Search .............. 424/279, 305, 317; 260/343.5; 560/107, 185, 256, 119; 562/501; 549/292

[56] References Cited

U.S. PATENT DOCUMENTS

| | | |
|---|---|---|
| 3,983,140 | 10/1977 | Endo et al. |
| 4,049,495 | 6/1978 | Endo et al. |
| 4,137,322 | 1/1979 | Endo et al. |
| 4,231,938 | 11/1980 | Monaghan et al. ............... 549/292 |
| 4,293,496 | 10/1981 | Willard et al. ..................... 562/501 |
| 4,294,846 | 10/1981 | Albers-Schonberg et al. .... 549/292 |
| 4,342,767 | 8/1982 | Albers-Schonberg ............. 549/292 |
| 4,351,844 | 9/1982 | Patchett et al. .................... 424/279 |
| 4,361,515 | 11/1982 | Terahara et al. ................... 562/501 |
| 4,376,863 | 3/1983 | Lam .................................... 549/292 |
| 4,387,242 | 6/1983 | Endo et al. ..................... 549/292 X |

FOREIGN PATENT DOCUMENTS

| | | |
|---|---|---|
| 55-009024 | 8/1980 | Japan . |
| 56-110618 | 1/1981 | Japan ................................ 424/311 |
| 2073199A | 10/1981 | United Kingdom ............... 562/501 |

OTHER PUBLICATIONS

F. M. Singer et al., Proc. Soc. Exper. Biol. Med., 102, 370, (1959).
Hulcher, Arch. Biochem. Biophys. 146, 422, (1971).
Brown et al., J. Chem. Soc., Perkin I, 1165, (1976).
Endo et al., J. Antibiotics, XXXII, 852, (1979).

*Primary Examiner*—Ethel G. Love
*Attorney, Agent, or Firm*—William H. Nicholson; Mario A. Monaco

[57] ABSTRACT

6(R)-[2-(8'-acyloxy-2'-methyl-6'-methyl (or hydrogen)-polyhydronaphthyl-1')-ethyl]-4(R)-hydroxy-3,4,5,6-tetrahydro-2H-pyran-2-ones are prepared by acylation of the corresponding 8'-hydroxy compounds. The products are strong inhibitors of the biosynthesis of cholesterol.

9 Claims, No Drawings

ANTIHYPERCHOLESTEROLEMIC COMPOUNDS

SUMMARY OF THE INVENTION

This is a continuation-in-part of copending application Ser. No. 217,640, filed Dec. 18, 1980, which is a continuation-in-part of copending application Ser. No. 175,460, filed Aug. 5, 1980, now abandoned, which in turn is a continuation-in-part of copending application Ser. No. 118,051, filed Feb. 4, 1980, (now abandoned).

This invention relates to a group of 6(R)-[2-(8'-acyloxy-2'-methyl-6'-methyl(or hydrogen)-polyhydronaphthyl-1')-ethyl]-4(R)-hydroxy-3,4,5,6-tetrahydro-2H-pyran-2-ones and to the hydroxy acid form of said pyranones, the pharmaceutically acceptable salts of said hydroxy acids and to the lower alkyl and phenyl, dimethylamino or acetylamino substituted lower alkyl esters of said hydroxy acid.

More specifically, this invention relates to a compound of the structure I in Table I, in which the dotted lines X, Y and Z represent possible double bonds, said double bonds being, when any are present, either X and Z together in combination or X, Y or Z alone; R represents 1-ethyl-1-methylpropyl, 1,1-diethylpropyl 1,1-dimethylethyl, 1,1-diethylbutyl, 1,1-dimethylpropyl, $C_{3-10}$ cycloalkyl, $C_{2-10}$ alkenyl, $C_{1-10}$ $CF_3$-, substituted alkyl, phenyl, halophenyl, phenyl-$C_{1-3}$ alkyl or substituted phenyl-$C_{1-3}$ alkyl, in which the substituent is halo, $C_{1-3}$ alkyl or $C_{1-3}$ alkoxy; and the free hydroxy acids of formula II formed by opening the lactone ring of formula I in Table I.

BACKGROUND OF THE INVENTION

It is known that certain mevalonate derivatives inhibit the biosynthesis of cholesterol, c.f. F. M. Singer et al, *Proc. Soc. Exper. Biol. Med.*, 102 370 (1959) and F. H. Hulcher, *Arch. Biochem. Biophys.*, 146, 422 (1971). Nevertheless, the activity of these known compounds has not always been found to be satisfactory, i.e. to have practical application.

Recently, Endo et al, reported (U.S. Pat. Nos. 4,049,495, 4,137,322 and 3,983,140) the production of fermentation products which were quite active in the inhibition of cholesterol biosynthesis. The most active member of this group of natural products, now called compactin, IIIa(R'=H) was reported by Brown et al. [*J. Chem. Soc. Perkin I* 1165 (1976)] to have a complex mevalonolactone structure.

More recently, Monaghan et al in U.S. Pat. No. 4,231,938, which is incorporated herein by reference, reported an inhibitor, designated MK-803 and having the structure $III_a$ (R'=CH$_3$) in Table I, which was isolated from an entirely different fermentation. Albers-Schonberg et al (U.S. Pat. No. 4,294,846) described a dihydro MK-803, designated $III_d$ (R'=CH$_3$) in Table I, of about equal potency to MK-803 isolated from the same fermentation as was MK-803. Patchett et al (U.S. Ser. No. 210,826, filed Dec. 1, 1980) describe dihydro and tetrahydro derivatives of MK-803 of different structures ($III_{b,c\ and\ e}$ (R'=CH$_3$) in Table I), prepared by the catalytic hydrogenation of MK-803. Willard (U.S. Pat. No. 4,293,496), describes the preparation of the 8-hydroxy derivatives ($IV_{a-e}$ (R'=CH$_3$) in Table I) which are the starting materials for the preparation of some of the novel compounds of this invention.

A tetrahydro analog $III_e$ (R'=H), of compactin was reported in published Japanese Application (Kokai) 55009-024.

Very recently a dihydro-analog of compactin of structure $III_d$ (R=H) was isolated from compactin fermentation broths as reported by Gullo et al, (U.S. application Ser. No. 207,508, filed Nov. 17, 1980).

The preparation of the starting material, $III_d$, $R^1$=CH$_3$) as mentioned previously, is described by Albers-Schonberg et al in U.S. Pat. No. 4,294,846, and is the product of the following fermentation with a strain of *Aspergillus terreus*, ATCC No. 20542, designated MF-4845 in the culture collection of MERCK & CO., Inc., Rahway, N.J.

PREPARATION OF COMPOUND $III_d$ (R'=CH$_3$)

A. Fermentation

A tube of lyophilized culture MF-4845 was opened aseptically and the contents suspended in an unbaffled 250 ml Erlenmeyer flask (seed flask) containing approximately 10 ml of the Medium which has the following composition:

| Medium | |
|---|---|
| Corn steep liquor | 5 g |
| Tomato paste | 40 g |
| Oatmeal | 10 g |
| Glucose | 10 g |
| Trace Element Solution | 10 g |
| Distilled water | 1000 ml |
| pH 6.8 with NaOH | |
| Trace Element Solution | |
| FeSO$_4$.7H$_2$O | 1000 mg |
| MnSO$_4$.4H$_2$O | 1000 mg |
| CuCl$_2$.2H$_2$O | 25 mg |
| CaCl$_2$.2H$_2$O | 100 mg |
| H$_3$BO$_3$ | 56 mg |
| (NH$_4$)$_6$Mo$_7$O$_{24}$.4H$_2$O | 19 mg |
| ZnSO$_4$.7H$_2$O | 200 mg |
| Distilled Deionized Water | 1000 ml |

The inoculated flask was incubated for 24 hours at 28° C. on a 220 rpm shaker (2 inch throw). An unbaffled 2 liter Erlenmeyer flask containing 500 ml of the medium was then inoculated with 10 ml of the first stage fermentation growth from the seed mixture. This too was shaken 24 hours at 28° C.

A 200 gallon stainless steel fermentation vat was then charged with 485 liters of a medium comprising:

| Cerelose | 4.5% wt/vol |
|---|---|
| Peptonized Milk | 2.5% wt/vol |
| Autolyzed yeast | 0.25% wt/vol |
| Polyglycol P2000 | 0.25% vol/vol | whose pH was adjusted to 7.0. This was sterilized 15 minutes at 121° C. One liter of the second stage above was then charged and the mixture was incubated at 85 rpm for 12 hours then at 130 rpm for 84 hours at 28° C. with an air flow of 5 cfm for 12 hours then 10 cfm for 84 hours.

B. Isolation

1. Extraction

Two batches of one hundred gallons of whole broth were combined, acidified with stirring to pH 4.1 by careful addition of 800 ml of concentrated hydrochloric acid, and extracted by addition of 75 gal of ethyl acetate and further stirring for two hours.

About 25 lbs of a silicaceous filter aid was then added and the total slurry was pumped through a 24-inch filter press. An additional 75 gal of ethyl acetate was used to wash the press cake and continue the extraction, by reversing the direction of pumping through the press four times. Then all of the wash solvent was discharged from the press and combined with the first filtrate. The two-phase filtrate was allowed to settle, and the water layer removed. The ethyl acetate layer was washed with 10 gal of deionized water, the phases were allowed to separate and the ethyl acetate extracts were concentrated under vacuum to a residue of about 10 gal.

2. Lactonization

Ethyl acetate extracts from an additional three hundred gal of broth were added to the above extract and the volume was reduced to about thirty gal by vacuum distillation. About fifty gal of toluene was added, and the batch was concentrated under vacuum to 32 gal; this step was repeated; then sufficient new toluene was added to bring the volume to 75 gal. Without vacuum, the batch was brought to reflux and maintained there for two hours, with a temperature over 106° C.

This solution was then concentrated under vacuum to a small volume, which was further concentrated to an oily residue in a large rotary evaporator under vacuum.

3. Chromatography on Silica Gel

The extract obtained above was flushed free of other solvents by addition of 2 gal of methylene chloride and reconcentration to an oil.

The oily residue was dissolved in about 5 gal of ethyl acetate-methylene chloride (30/70; v/v) mixture, and a slurry was made by addition of 2.8 kg of silica gel.

The slurry was loaded as a level layer on the top of a 12 in.×50 in. silica gel column packed in the same solvent mixture.

Elution was with ethyl acetate-methylene chloride (40/60; v/v) at 800 ml/min. A forerun of 10 gal, then further fractions of 4 gal each were collected.

Fractions 6–10 inclusive were concentrated under vacuum to an oily residue which was dissolved in hot ethyl acetate, treated with decolorizing carbon, filtered hot, and cooled. Crystals of Compound $III_a$ ($R'=CH_3$) were filtered off and the mother liquors were concentrated to an oil for further chromatography.

4. Rechromatography on Silica Gel

Mother liquor residues from similar broth extract work-ups equivalent to an additional 600 gal of fermentation production were combined with the above in methylene chloride solution. One-half of this solution was taken for further silica gel chromatography. A small aliquot showed a total solids content of 325 g. The solution was treated with 40 g of decolorizing carbon, filtered, and the cake rinsed with methylene chloride. The combined filtrate and washings were concentrated under vacuum to an oily residue. This was redissolved in 800 ml of ethyl acetate/methylene chloride (30/70; v/v) and slurried with 225 g of silica gel. The slurry was loaded on top of a 14×36 cm column bed of silica gel packed in the same solvent mixture. Development was with ethyl acetate/methylene chloride (40/60; v/v). A forecut of three liters was set aside; then fractions of 800 ml each were collected.

5. Chromatography on Reverse-phase Packing

Forty ml from fraction 12 of the above chromatography were concentrated to an oil weighing 500 mg and the oil redissolved in 5 ml acetonitrile. This acetonitrile solution was charged to a 5/8" OD by 6 ft long stainless steel chromatography column packed with preparative reverse-phase liquid chromatography column packing material "Bondapak C18/PorasilB" (Waters Associates, Inc., Milford, Mass. 01757). The column was eluted with a mixture consisting of (v/v) 55% acetonitrile and 45% 0.05 M ammonium phosphate pH3. The elution volume between 1360 ml and 1700 ml was combined on the basis of refractive index detection. The organic solvent was removed in vacuo and the residual aqueous solution extracted with ethyl acetate. In vacuo removal of the ethyl acetate left 120 mg of compound which crystallized from a concentrated acetonitrile solution yielding crystals of Compound $III_d$ ($R'=CH_3$), m.p. 129°–131° C.

PREPARATION OF COMPOUNDS $III_{b, c, e}$

Starting materials $III_b$, $III_c$ and $III_e$ ($R'=CH_3$) as mentioned above are described in U.S. application, Ser. No. 210,826, filed Dec. 1, 1980 by Patchett et al., in accordance with the following Flow Sheet and preparative methods extracted therefrom.

The desmethyl analogs, $III_b$, $III_c$ and $III_e$ ($R'=H$) are obtained substantially as described by Patchett et al. but starting with $III_a$ ($R'=H$) in each case.

For the preparation of $III_e$ it is advantageous to reduce $III_d$ inasmuch as the desired trans fusion of the perhydronaphthalene ring, present in the starting materials, is retained in the final product, and the need to separate isomers is avoided.

FLOW SHEET

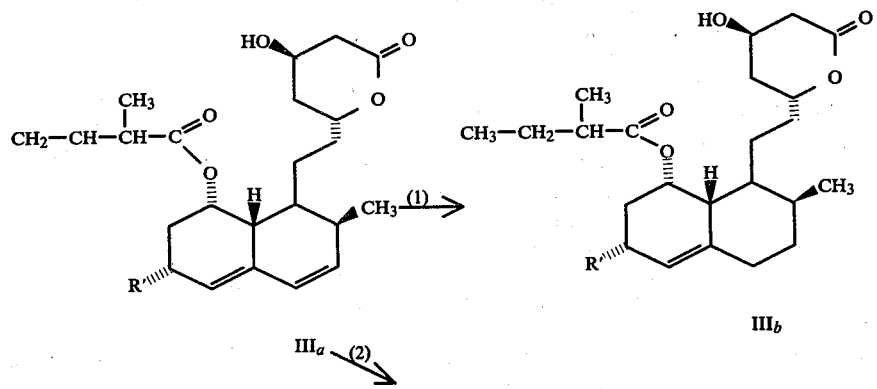

FLOW SHEET

-continued

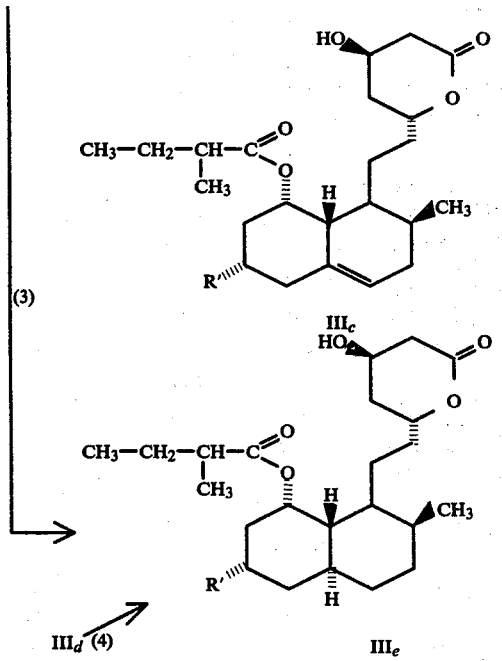

Reactions and Reagents

1. Hydrogenation at about 20°–75° C. and about atmospheric pressure to about 4 atmospheres over tris-(triphenylphosphine)chlororhodium in an aromatic solvent such as benzene, toluene or xylene, preferably toluene. Preferred conditions are about 40° C. and about 2–7 atmospheres in toluene.
2. Hydrogenation at about 20°–25° C. and about atmospheric pressure over 5% palladium on calcium carbonate in a lower alkanol such as a $C_{1-3}$ alkanol, especially ethanol.
3. Hydrogenation at about 20°–25° C. and atmospheric pressure over platinum oxide in ethyl acetate.
4. Hydrogenation at about 20°–25° C. and atmospheric pressure over 10% Palladium on charcoal in ethyl acetate.

Preparation of 6α-[2-(8'-β-2-(S)-methylbutyryloxy-2'β,6'α-dimethyl-1',2',3',4',6',7',8',8'a-octahydronaphthyl-1)ethyl]-4β-hydroxy-3,4,5,6-tetrahydro-2H-pyran-2-one, III$_b$ (R'=CH$_3$)

A mixture of 50 mg (0.1236 mmol) of Compound III$_a$ (R'=CH$_3$) and an equal molar amount (114.35 mg, 0.1236 mmol) of tris(triphenylphosphine)chlororhodium in 10 ml of dry toluene was hydrogenated at room temperature for 6 days, with a total uptake of 14.6 ml of hydrogen. The mixture was evaporated in vacuo to dryness. The red residue was subjected to preparative thin-layer chromatography on silver nitrate impregnated silica plates and was developed twice in the 10% ethyl acetate-ether system. The yield of Compound III$_b$ (R'=CH$_3$) was 22.3 mg.

Mass spectrum (M/e): 406 (m+), 304 (m-102), 286 (m-102-18)

nmr (CDCl$_3$, 300 MHz): δ 4.37 (m, 1H), 4.60 (m, 1H), 5.34 (d of t, J=2.5 Hz, 1H), 5.41 (m, 1H)

Preparation of 6α-[2-(8'β-2-(S)-methylbutyryloxy-2'β,6'α-dimethyl-1',2',3',5',6',7',8',8'a-octahydronaphthyl-1)ethyl]-4β-hydroxy-3,4,5,6-tetrahydro-2H-pyran-2-one, III$_c$ (R'=CH$_3$)

A solution of 80.91 mg (0.2 mmol) of Compound III$_a$ (R'=CH$_3$) in 10 ml of absolute ethanol, in the presence of an equal weight of 5% Pd on CaCO$_3$ was hydrogenated at 1 atmosphere until an uptake of one mole equivalent of hydrogen was observed. The catalyst was then removed by filtration and the filtrate was evaporated to dryness (81 mg). After a purification by preparative thin-layer chromatography to remove a small amount of by-product tetrahydro compound, 72 mg of the 1,4 reduction product III$_c$ (R'=CH$_3$) was isolated.

Mass spectrum (M/e): 406 (m+), 304 (m-102), 286 (304-H$_2$O)

nmr (CDCl$_3$, 300 MHz): δ 4.38 (m, 1H), 4.64 (m, 1H), 5.28 (d of t, J=3.5 Hz, 1H), 5.48 (m, 1H)

Preparation of 6α-[2-(8'β-2(S)-methylbutyryloxy-2'α,baβ-dimethyl-1',2',3',4',4'aα,5',6',7',8',8'a-decahydronaphthyl-1)ethyl]-4β-hydroxy-3,4,5,6-tetrahydro-2H-pyran-2-one, III$_e$ (R'=CH$_3$)

A solution of 80.91 mg (0.2 mmol) of Compound III$_a$ (R'=CH$_3$) in 10 ml of ethyl acetate was hydrogenated in the presence of an equal weight of platinum oxide at one atmosphere. An exact 2 mole equivalent of hydrogen was consumed within 1 hour. The catalyst was removed by filtration and the filtrate was concentrated to dryness to give an oil. The cis and trans isomers were separated by preparative thin-layer chromatography on silica gel plates (10% ethyl acetate-ether system, bands detected by water spray). The trans isomer III$_e$ (R'=CH$_3$) appears as the more polar spot, compared to the cis isomer, and 60 mg was isolated.

Mass spectrum (M/e): 408 (m+), 323 (m-85), 306 (m-102)

nmr (CDCl$_3$, 300 MHz): δ 4.36 (broad singlet, 1H), 4.59 (m, 1H), 5.19 (d of t, J=2.5 Hz, 1H)

Fermentative Production of Compound III$_d$ (R'=H)

A. Fermentation

A natural isolate of *Penicillium citrinum*, NRRL 8082 was used to prepare a yeast-malt extract (YME) slant which was incubated for 2 weeks at 28° C.

A portion (1/5) of the slant (MF-4870a) was used to inoculate each of 5 unbaffled seed flasks (250 ml) containing 44 ml of KF seed medium with CaCl$_2$. They were incubated for 3 days at 28° C., and 220 rpm. A portion of the seed growth (about 1.5 ml) was used to inoculate each of 100 production medium flasks (250 ml unbaffled) containing 40 ml of LM Production Medium Without Malt Extract. The production flasks were incubated for 4 days at 25° C.

Another group of production medium flasks (140), each containing 40 ml of LM Production Medium Without Modification were inoculated and incubated under the same conditions as previously described. The broths from both fermentations were combined.

The various media employed in the foregoing fermentations are:

| YME Slant | |
|---|---|
| Dextrose | 4 g./l. |
| Malt Extract | 10 g./l. |
| Yeast Extract | 4 g./l. |
| Agar | 20 g./l/ |
| Dist. Water | to 1 liter |
| pH | 7.0 |
| KF Seed Medium with CaCl$_2$ | |
| CaCl$_2$ | 10 g |
| Corn steep liquor | 5 g |
| Tomato paste | 40 g |
| Oatmeal | 10 g |
| Cerelose | 10 g |
| Trace Element Mix | 10 ml |
| Distilled water | 1000 ml |
| pH | 6.8 |
| Trace Element Mix | |
| FeSO$_4$.7H$_2$O | 1 g |
| MnSO$_4$.4H$_2$O | 1 g |
| CuCl$_2$.2H$_2$O | 25 mg |
| CaCl$_2$ | 100 mg |
| H$_3$BO$_3$ | 56 mg |
| (NH$_4$)$_6$Mo$_7$O$_{24}$.4H$_2$O | 19 mg |
| ZnSO$_4$.7H$_2$O | 200 mg |
| Distilled Water | 1000 ml |
| LM Production Medium Without Malt Extract | |
| Dextrose | 20 g |
| Glycerol | 20 ml |
| Ardamine pH | 10 g |
| CoCl$_2$.6H$_2$O | 8 mg |
| Polyglycol p 2000 | 0.25% |
| Distilled Water | 1000 ml |
| pH | 7.0 |
| LM Production Medium Without Modification | |
| Dextrose | 20 g |
| Glycerol | 20 ml |
| Ardamine pH | 10 g |
| Malt Extract | 20 g |
| CoCl$_2$.6H$_2$O | 8 mg |
| Polyglycol p 2000 | 0.25% |
| Distilled Water | 1000 ml |
| pH | 7.0 |

B. Isolation

The combined whole broth (10.3 liters) was filtered and the mycelia cake was washed with 2.5 liters of deionized water. The combined filtrate and wash was adjusted to pH 4.0 with 1 N hydrochloric acid. The aqueous solution was extracted with 7 liters of ethyl acetate and the extract was back-extracted with 3×2 liters of aqueous sodium hydroxide solution. The combined sodium hydroxide extract was adjusted to pH 3.8 with 1 N hydrochloric acid and extracted with 2 liters and 1 liter of ethyl acetate. The combined ethyl acetate solution was dried over anhydrous Na$_2$SO$_4$, filtered and concentrated to dryness. The oily residue was dissolved in toluene and refluxed for 1 hour. The toluene solution was concentrated to dryness and the residue was dissolved in 18 ml of a mixture of n-hexane/toluene/methanol (4/1/1 by volume). This solution was loaded onto a 30 mm (ID)×40 cm. Sephadex LH-20 column equilibrated in the same solvent system. After eluting with 300 ml of solvent, a 10 ml fraction was obtained which was concentrated to an oil. High performance liquid chromatography (HPLC) on an ES Industries Chromega ® column (9 mm×50 cm) using a mixture of acetonitrile/water (60/40 by volume) as the eluting solvent yielded 45 mg of dihydrocompactin (Compound III$_d$, R'=H), m.w. 392.2560 by mass spectrum (calculated for C$_{23}$H$_{36}$O$_5$, 392.2558).

In KBr, the major IR peaks obtained from a Fourier Transform-IR (FTIR, Nicolet, Model 7199) are at 1724, 1704, 1258, 1078 and 1070 cm$^{-1}$. Of significance is a peak at 3005 cm$^{-1}$ and the absence of a peak at 3030 cm$^{-1}$.

A nuclear magnetic resonance spectrum was obtained in CDCl$_3$, ~1 mg/0.5 ml) on a Varian SC-300 superconducting nmr spectrometer. The following are the peak positions given in ppm (δ) relative to internal tetramethylsilane (TMS).

| δ | Assignment |
|---|---|
| 5.62 d,d,d (2.17, 4.5, 10.0) | H$_{3'}$ (d?) |
| 5.43 d (10) | H$_{4'}$ (c?) |
| 5.20 m | H$_{8'}$ |
| 4.63 m | H$_6$ |
| 4.39 m | H$_4$ |
| 2.75 d,d (17.5, 5.5) | |
| 2.63 d,d,d (17.5, 4.0, 1.5) | 3-CH$_2$ |
| 2.39 m | CH$_3$HCC⩽$^O$ |
| 2.29 m | H$_{4a'}$ + H$_{5'}$ |
| 1.14 d | CH$_3$CHC⩽$^O$ |
| 0.90 t | CH$_3$CH$_2$ |
| 0.84 d | CH$_3$H$_{2'}$ | d: doublet;
m: multiplet;
t: triplet

The evidence indicates the structure to be:

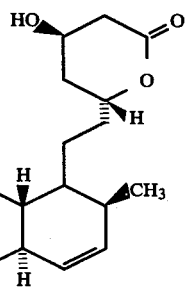

PREPARATION OF COMPOUNDS IV$_{a-e}$

The starting materials, the 8'α-hydroxy compounds IV$_{a-e}$ (R'=CH$_3$) described by Willard (U.S. Pat. No. 4,293,496) are prepared from the various 8'-esters described by Monaghan et al (III$_a$, R'=CH$_3$), Albers-Schonberg et al (III$_d$, R'=CH$_3$) and Patchett et al (III$_{b,c,e}$, R'=CH$_3$) by heating them with lithium hydroxide solution for extended periods. The pyranone ring readily opens but the removal of the side chain acyl group is not easily effected. The heating must be prolonged and/or pressure must be used. An inert atmosphere is also helpful.

In the case of the Compounds III$_{a-e}$ (R'=H) the saponification of the 8'-esters is much more facile proceeding to completion in about 20 hours.

The 8'-hydroxy products are isolated by acidification and extraction with organic solvents which provides the trihydroxy acid form, in which the pyranone ring is still opened. These trihydroxy acids are relactonized by heating a solution of the acid in an appropriate organic solvent such as benzene or toluene in an apparatus permitting continuous separation of the water formed.

The Compound IV$_a$ (R'=H) is known as ML-236A as reported by Endo et al in U.S. Pat. No. 3,983,140.

In their lactone form, these alcohols are the compounds of Formula IV$_{a-e}$ in Table I and are prepared as described in the following preparations.

Preparation of 6(R)-[2-(8'(S)-hydroxy-2'(S),6'(R)-dimethyl-1',2',6',7',8',8'a(R)-hexahydronaphthyl-1'(S))ethyl]-4(R)-hydroxy-3,4,5,6-tetrahydro-2H-pyran-2-one, IV$_a$ (R'=CH$_3$)

A mixture of 8.0 g. (19.78 mmole) of MK-803 (III$_a$, R'=CH$_3$) and 8.31 g (197.8 mmole) of LiOH.H$_2$O in 600 ml of water was stirred at reflux under a nitrogen atmosphere for 56 hours. The reaction mixture was cooled to 0° and treated, with stirring, with 20 ml of concentrated hydrochloric acid. The mixture was then extracted with three 250-ml portions of ether and the combined extracts were washed successively with three 200-ml portions of water and then 200 ml of saturated brine. After drying over MgSO$_4$, this organic solution was filtered and the solvent evaporated in vacuo to give an oily residue. This residue was dissolved in 200 ml of toluene and heated at reflux under a nitrogen atmosphere for 2 hours with continuous separation of water to effect relactonization. Evaporation of the toluene and trituration of the residue with hexane gave 5.15 g (81%) of the title compound IV$_a$ (R'=CH$_3$) as a white solid which did not require further purification.

An analytical sample was prepared by recrystallization of a portion of this material from butyl chloride to give white clusters: m.p. 128°–131° (vacuum);

NMR(CDCl$_3$) δ0.87 (d,3,J=7 Hz, CH$_3$), 1.16 (d,3,J=7 Hz, CH$_3$), 2.64 (m,2,pyran C$_3$H's), 4.27 (brm,1, naphthalene C$_8$H), 4.37 (m,1,pyran C$_4$H), 4.71 (m,1,pyran C$_6$H), 5.56 (m,1, naphthalene C$_5$H), 5.79 (dd,1, J=6,10 Hz, naphthalene C$_3$H), 6.03 (d,1,J=10 Hz, naphthalene C$_4$H); IR (CHCl$_3$) 3400 (OH), 1725 (C=O), 1240, 1120, 108 cm$^{-1}$.

Anal. Calcd for C$_{19}$H$_{28}$O$_4$.0.1C$_4$H$_9$Cl C, 70.67; H, 8.84. Found: C, 70.77; H, 8.75.

Alternative preparation of 6(R)-[2-[8'-(S)-hydroxy-2'(S),6'(R)-dimethyl-1'2',6',7',8',8'a(R)-hexahydronaphthyl-1'(S)]ethyl]-4(R)-hydroxy-3,4,5,6-tetrahydro-2H-pyran-2-one, IV$_a$ (R'=CH$_3$)

A suspension of 188 mg (0.463 mmol) of MK-803 (III$_a$, R'=CH$_3$) in 5 ml (5 mmol) of aqueous 1 N LiOH solution is shaken for 12 hours at 135° in a 30 ml stainless steel pressure vessel. The cooled reaction mixture is acidified with 1 M H$_3$PO$_4$ and extracted with ethyl acetate. The ethyl acetate solution is dried (MgSO$_4$) and filtered and the solvent is evaporated. The residue is dissolved in 20 ml of toluene which is heated to reflux for 4 hours in a Dean-Stark apparatus to effect relactonization. Evaporation of the toluene gives the title compound.

Preparation of alcohols IV$_a$ (R'=H) and IV$_b$, IV$_c$, IV$_d$, and IV$_e$ (R'=H or CH$_3$)

Following essentially either procedure described above but substituting an equivalent amount of esters III$_a$ (R'=H) or III$_b$, III$_c$, III$_d$, or III$_e$ (R'=H or CH$_3$), for III$_a$ (R'=CH$_3$) used therein the corresponding alcohols IV$_a$(R'=H), IV$_b$, IV$_c$, IV$_d$ and IV$_e$ (R'=H or CH$_3$) are respectively obtained.

DESCRIPTION OF THE INVENTION

We have found that the 8'-hydroxy compounds of Structure IV can be acylated to give a new class of 8'-acyloxy compounds of the structure defined by Formulas I and II and the definitions thereunder. These new compounds are not formed in the fermentations described by Endo, Monaghan, Albers-Schonberg or Gullo. They are inhibitors of cholesterol synthesis in vivo.

The absolute configuration of these compounds is known from X-ray diffraction. Table I provides a convenient tabulation of these structures and their stereochemical relationship. The reference numerals to the various compounds, including those of the various series of polyhydronaphthyl structures, remain the same throughout these specifications and are so used. Each of the esters I$_{a-e}$ (R'=CH$_3$), of this invention contains seven or eight chiral centers. The relative and absolute configuration of these asymmetric centers is as depicted in Table I. More specifically, for ester I$_a$ (R'=CH$_3$), the Cahn, Ingold, Prelog designations for the absolute configurations are 4(R), 6(R), 1'(S), 2'(S), 6'(R), 8'(S) and 8a'(R) [R. S. Cahn, C. Ingold and V. Prelog, *Angew, Chem. Int. Ed.*, 5, 385 (1966)].

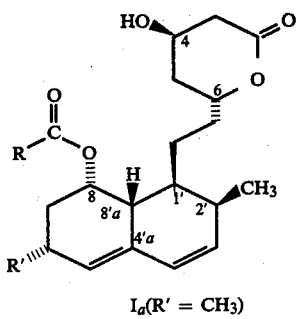

I$_a$(R' = CH$_3$)

As is indicated in the formulas I$_{a-e}$, all of these compounds have the same spatial orientation of groups at each chiral carbon atom and therefore belong to the same stereochemical series. The R-S designation for each center may not be identical to that found for the ester I$_a$ (R'=CH$_3$) because of the details of the sequence rules used for determining that designation. In the two esters I$_d$ and I$_e$ which have an additional chiral carbon atom not present in ester I$_a$, the hydrogen atom at 4a' is in the down (or α) orientation as depicted in Table I, giving a trans ring junction.

TABLE I
THE COMPOUNDS OF THIS INVENTION AND THIER STEREO-RELATIONSHIP

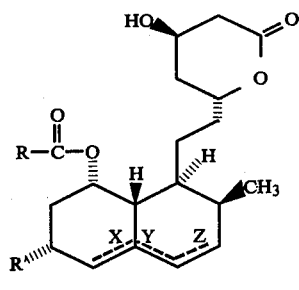

I$_{a-e}$

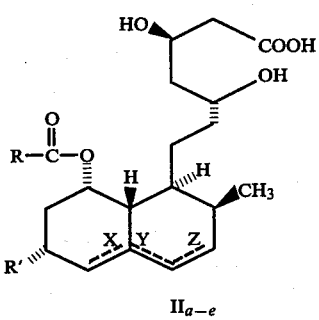

II$_{a-e}$

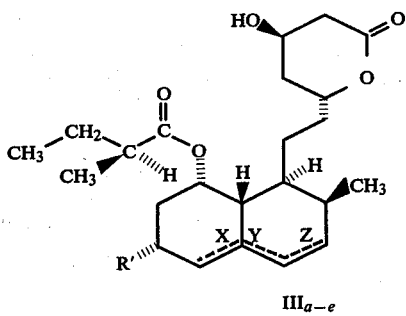

III$_{a-e}$

TABLE I-continued
THE COMPOUNDS OF THIS INVENTION AND THIER STEREO-RELATIONSHIP

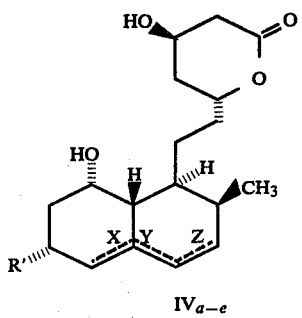

IV$_{a-e}$

R' = H or CH$_3$
STEREOCHEMISTRY OF THE HYDRONAPHTHYL SERIES

| Series | Double Bonds Present | Structure |
|---|---|---|
| a | X and Z | 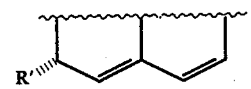 |
| b | X | 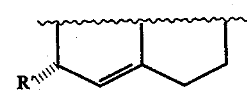 |
| c | Y | 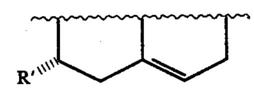 |
| d | Z | 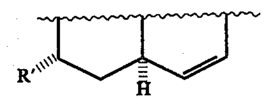 |
| e | None | 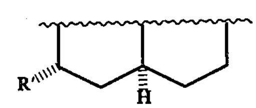 |

The compounds of this invention are useful as antihypercholesterolemic agents for the treatment of atherosclerosis, hyperlipemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 10 to 100 mg) given in three of four divided doses. Higher doses may be favorably applied as required.

The compounds of this invention also have useful anti-fungal activities. For example, they may be used to control strains of Penicillium sp., *Aspergillus niger*, Cladosporium sp., *Cochiliobolus miyabeanus* and *Helminthosporium cynodnotis*. For those utilities they are admixed with suitable formulating agents, powders, emulsifying agents or solvents such as aqueous ethanol and sprayed or dusted on the plants to be protected.

The preparation of the compounds of this invention is described in Flow Sheet A.

FLOW SHEET A

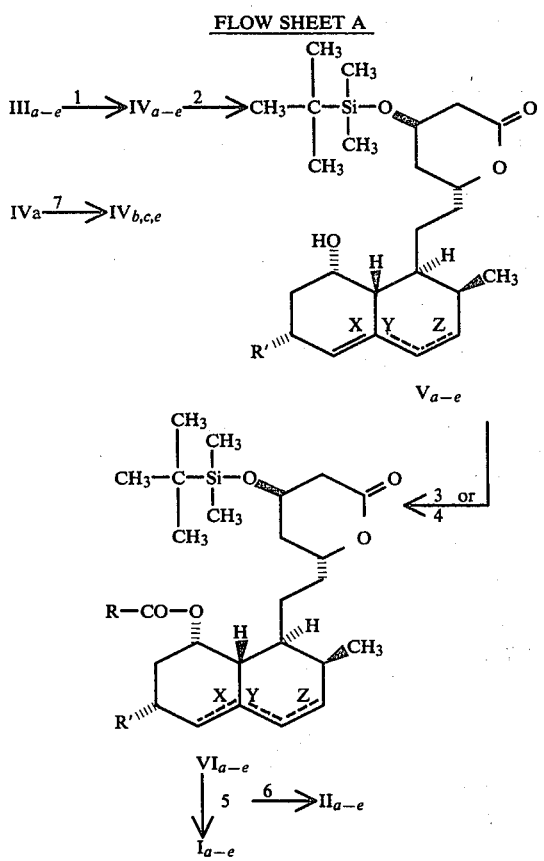

Definitions
  X, Y, Z, R and R' as defined in specification and series a-e as defined in Table I.

Reactions
(1) Lithium hydroxide, heat, acidify, and lactonize
(2) t-Butyldimethylchlorsilane and imidazole in DMF at ambient temperatures in an inert atmosphere.
(3) Treatment with RCOCl and 4-dimethylaminopyridine in pyridine solution preferably under inert atmosphere.
(4) Treatment with RCOOH and N,N'-dicyclohexylcarbodiimide and 4-pyrrolidinopyridine in dichloromethane, preferably under an inert atmosphere.
(5) Three equivalents of tetrabutylammonium fluoride and four equivalents of acetic acid per equivalent of ester in THF, preferably in an inert atmosphere.
(6) Aqueous alkali followed by careful acidification with dilute acid.
(7) See Reactions and Reagents and Flow Sheet for synthesis of III$_{b,c,e}$.

In the novel process of this invention the 4-hydroxyl on the pyranone ring, of alcohols IV$_{a-e}$ is first protected with a t-butyldimethylsilyl group by reaction with t-butyldimethylchlorosilane in an inert atmosphere at ambient temperatures in the presence of an acid acceptor such as imidazole to provide the protected alcohols V$_{a-e}$. The 8-hydroxyl on the polyhydronaphthyl ring is then acylated in one of two ways. The first comprises treatment with the acid chloride of the desired acyl group in pyridine in the presence of 4-dimethylaminopyridine as a catalyst. The second comprises treatment of the 8'-polyhydronaphthol with the free acid of the desired acyl group and a carbodiimide such as N,N'-dicyclohexylcarbodiimide with 4-pyrrolidinopyridine as a catalyst in dichloromethane. These procedures give the protected esters VI$_{a-e}$. The removal of the silyl protecting group from the 4-hydroxyl of the pyranone ring is then carried out, using three equivalents of tetrabutylammonium fluoride and four equivalents of acetic acid per equivalent of esters VI$_{a-e}$, to give the desired compounds I$_{a-e}$. The ratio of reagents in this last reaction is critical to the yield of the process and the purity of the products.

The acyl groups thus put on the 8'-hydroxyl are those in which R in I$_{a-e}$ is:
(1) 1,1-diethylpropyl, 1-ethyl-1-methylpropyl, 1,1-dimethylethyl, 1,1-diethylbutyl, 1,1-dimethylpropyl,
(2) $C_{3-10}$cycloalkyl,
(3) $C_{2-10}$alkenyl,
(4) $C_{1-10}$ $CF_3$-substituted alkyl,
(5) phenyl,
(6) halophenyl, wherein halo is chloro, fluoro, bromo or iodo,
(7) phenyl-$C_{1-3}$ alkyl,
(8) substituted phenyl-$C_{1-3}$ alkyl in which the substituent is halo, such as fluoro, chloro, bromo, or iodo, $C_{1-3}$ alkyl or $C_{1-3}$ alkoxy.

It is preferred that R' be $CH_3$.

Preferred definitions of R, are: 1,1-diethylpropyl, 1-ethyl-1-methylpropyl, 1,1-dimethylethyl, 1,1-diethylbutyl, 1,1-dimethylpropyl, $C_{3-10}$ cycloalkyl, $C_{3-10}$ alkenyl in which the unsaturation is not in conjunction with the carbonyl.

Preferred species are those wherein R is 1,1-dimethylpropyl. And it is also preferred that none of X, Y or Z is a double bond.

Compounds I$_{a-e}$ can be hydrolyzed with bases such as NaOH to yield the salts such as the sodium salt of Compounds II$_{a-e}$. The use of bases with other pharmaceutically acceptable cations affords salts of those cations. Careful acidification of the salts affords the hydroxy acids II$_{a-e}$ which revert to Compounds I$_{a-e}$ at acidic pH. Treating Compound I$_{a-e}$ under acidic or basic catalysis with methanol, ethanol, propanol, or butanol or with phenyl-, dimethylamino-, or acetylamino-alkanols yields the corresponding esters of Compounds II$_{a-e}$ which also form a part of this invention.

The pharmaceutically acceptable salts of this invention include those formed from cations such as sodium, potassium, aluminum, calcium, lithium, magnesium, zinc and tetramethylammonium as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane.

EXAMPLE 1

6(R)-[2-(8'(S)-2'',2''-dimethylpropanoyloxy-2'(S),6'(R)-dimethyl-1',2',6',7',8',8'a(R)-hexahydronaphthyl-1'(S))-ethyl]-4(R)-hydroxy-3,4,5,6-tetrahydro-2H-pyran-2-one

Step A: Preparation of 6(R)-[2-(8'(S)-hydroxy-2'(S)-6'(R)-dimethyl-1',2',6',7',8',8'a(R)-hexahydronaphthyl-1'(S))ethyl]-4(R)-(dimethyl-tert-butylsilyloxy)-3,4,5,6-tetrahydro-2H-pyran-2-one, $V_a$ (R'=CH$_3$)

A mixture of the alcohol IV$_a$ (R'=CH$_3$) (18.3 g, 57.1 mmol), 21.5 g (142.8 mmol) of tert-butyldimethylchlorosilane and 19.4 g (285.6 mmol) of imidazole in 200 ml of N,N-dimethylformamide was stirred at 20° under a nitrogen atmosphere for 18 hours. The reaction mixture was then diluted with 1500 ml of ether and washed successively with water, 2% aqueous hydrochloric acid, water and saturated sodium bicarbonate. The ether solution was dried over MgSO$_4$, filtered and reduced to a volume of 1 L. After addition of 600 ml of hexane, the volume was reduced to 600 ml on a steam bath. The product crystallized at room temperature; after isolation and air drying this provided 13.7 g of a white cottony solid. The mother liquors are reduced to 250 ml and a second crop of crystals was isolated after this solution stood at 0° overnight. The combined yield was 17.13 g (69%) of the title compound as a white cottony solid: mp 142°–144° (vac); NMR (CDCl$_3$) δ0.10 (s,6,(CH$_3$)$_2$Si), 0.90 (s,9,(CH$_3$)$_3$CSi), 1.19 (d,3,J=7 Hz, CH$_3$), 2.58 (d, 2,J=4 Hz,pyran C$_3$H's), 4.3 (m,2,pyran C$_4$H and naphthalene C$_8$H) 4.70 (m, 1, pyran C$_6$H), 5.57 (m,1,naphthalene C$_5$H), 5.58 (dd,1,J=6,10 Hz, naphthalene C$_3$H), 6.03 (d,1, J=10 Hz,naphthalene C$_4$H).

Anal. Calcd. for C$_{25}$H$_{42}$O$_4$Si: C, 69.08, H, 9.74. Found: C, 69.46; H, 9.83.

Step B: Preparation of 6(R)-[2-(8'(S)-2'',2''-dimethylpropanoyloxy-2'(S),6'(R)-dimethyl-1',2',6',7',8',8'a(R)-hexahydronaphthyl-1'(S))ethyl]-4(R) (dimethyl-tert-butylsilyloxy)-3,4,5,6-tetrahydro-2H-pyran-2-one, VI$_a$ (R'=CH$_3$)

A solution of 6.0 g (13.8 mmol) of the alcohol V$_a$ (R'=CH$_3$) from Step A and 200 mg of 4-dimethylaminopyridine in 50 ml of pyridine was cooled to 0° under a nitrogen atmosphere. To this stirred solution was added 6.8 ml (6.65 g, 55.2 mmol) of pivaloyl chloride over 15 minutes. The reaction mixture was stirred at 0° for 1 hour and then at 20° for 4 days. The reaction mixture was diluted with 750 ml of ether and washed with 2% aqueous hydrochloric acid until the wash was acidic and then with saturated NaHCO$_3$ solution. After drying over MgSO$_4$ the solution was filtered and evaporated to give 7.81 g of the title compound as a light orange oil: NMR (CDCl$_3$) δ0.09 (s,6(CH$_3$)$_2$Si), 0.88 (s,9,(CH$_3$)$_3$CSi), 1.28 (s,9, (CH$_3$)$_3$CCO$_2$—), 2.57 (d,2,J=4 Hz, pyran C$_3$H's), 4.32 (m, 1, pyran C$_4$H), 4.63 (m,1, pyran C$_6$H), 5.34 (m, 1, naphthalene C$_8$H), 5.54 (m,1, naphthalene C$_5$H), 5.78 (dd, 1, J=6, 10 Hz, naphthalene C$_3$H), 6.03 (d, 1,J=10 Hz, naphthalene C$_4$H).

Employing the procedure substantially as described in Example 1, Step B, but substituting for the pivaloyl chloride used therein, an equimolecular amount of the acid chloride of structure R—COCl described in Table II, there are prepared the esters of structure VI$_a$ (R'=CH$_3$) also described in Table II.

TABLE II

| R—C(=O)—O— | NMR(CDCl$_3$,δ) |
|---|---|
| 4-F-C$_6$H$_4$—CO$_2$— | 7.10 (t,2,J=8 Hz,p-FPh-) 8.03 (dd,2,J=5,8 Hz,p-FPh-) |
| CH$_3$CO$_2$— | 2.02 (s,3,CH$_3$CO$_2$—) |
| CH$_3$CH(CH$_3$)CH$_2$C(=O)O— | 1.19 (d,J=7 Hz,α-CH$_3$ ester) 1.21 (d,J=7 Hz,α-CH$_3$ ester) Total 3H |
| (CH$_3$)$_2$CHCH$_2$CO$_2$— | 0.83 (d,6,J=6 Hz,(CH$_3$)$_2$CH—) |
| (CH$_3$)$_2$CHCO$_2$— | 1.13 (d,6,J=6 Hz(CH$_3$)$_2$CH) |
| CH$_3$(CH$_2$)$_3$CO$_2$— | 0.95 (t,3,J=7 Hz,CH$_3$—(CH$_2$)$_3$— |
| Adamantyl—CO$_2$— | 1.60–2.08 (m,15,Adamantyl) |
| CH$_3$(CH$_2$)$_6$CO$_2$— | |
| C$_6$H$_{11}$CO$_2$— | |

| R—C(=O)—O— | |
|---|---|
| CH$_2$=CH—CO$_2$— | (CH$_3$)$_2$C=CH—CO$_2$— |
| CF$_3$(CH$_2$)$_2$CO$_2$— | |
| C$_6$H$_5$CO$_2$— | |
| 4-ClC$_6$H$_4$CO$_2$— | |
| 2,4-F$_2$C$_6$H$_3$CO$_2$— | CH$_2$=C(CH$_3$)CH$_2$CO$_2$— |
| C$_6$H$_5$(CH$_2$)$_3$CO$_2$— | |
| 4-FC$_6$H$_4$CH$_2$CO$_2$— | |
| 2,4-F$_2$C$_6$H$_3$CH$_2$CO$_2$— | CH$_3$(CH$_2$)$_8$CO$_2$— |
| 4-ClC$_6$H$_4$CH$_2$CO$_2$— | |
| 4-FC$_6$H$_4$(CH$_2$)$_3$CO$_2$— | |
| CF$_3$CH(CH$_3$)CH$_2$CO$_2$— | CH$_3$CH(H)(CH$_3$)CO$_2$— |

Step C: Preparation of 6(R)-[2-(8'-(S)-2'',2'''-dimethylpropanoyloxy-2'(S),6'(R)-dimethyl-1',2',6',7',8',8'a(R)-hexahydronaphthyl-1'(S))ethyl]-4(R)-hydroxy-3,4,5,6-tetrahydro-2H-pyran-2-one, I$_a$ (R'=CH$_3$)

To a solution of 10.0 g (31.7 mmol) of Bu$_4$N$^+$F$^-$·3-H$_2$O and 2.4 ml (2.5 g, 42.3 mmol) of acetic acid in 50 ml of tetrahydrofuran was added 7.81 g (13.8 mmol) of the silyl ether VI$_a$ (R'=CH$_3$) from Step B in 50 ml tetrahydrofuran. This mixture was stirred at 20° under a nitrogen atmosphere for 18 hours. The reaction mixture was diluted with 700 ml of ether and washed successively with 2% aqueous hydrochloric acid, water and saturated aqueous NaHCO$_3$. The organic solution was dried (MgSO$_4$) and filtered. Evaporation of the solvent left 6.45 g of an off-white solid. This material was crystallized from 100 ml of butyl chloride and the isolated crystals were dried at 35°/0.01 mm for four hours to give 4.0 g (72%) of the title compound as nearly white needles: mp 167.5°–170.5° (vac); NMR (CDCl$_3$) δ0.88 (d,3,J=7 Hz,CH$_3$), 1.08 (d,3,J=7 Hz, CH$_3$), 1.19

(s,9,(CH$_3$)$_3$C), 2.67 (d,2,J=4 Hz, pyran C$_3$H's), 4.39 (m,1,pyran C$_4$H), 4.65 (m,1,pyran C$_6$H), 5.36 (m,1,naphthalene C$_8$H) 5.55 (m,1,naphthalene C$_5$H), 5.80 (dd,1,J=6,10 Hz, naphthalene C$_3$H), 6.04 (d,1,J=10 Hz, naphthalene C$_4$H); HPLC (4.6 mm.×25 cm Partisil 10 PAC, 10% isopropanol/hexane, 4 ml/min) retention time 4.4 min.

Anal. Calcd. for C$_{24}$H$_{36}$O$_5$: C, 71.25; H, 8.97. Found: C, 71.40; H, 8.93.

Employing the procedure of Example 1, Step C, but substituting for the 2,2-dimethylpropanoyloxysilyl ether Compound VI$_a$ (R'=CH$_3$) used therein, an equimolecular amount of the other esters of structure VI$_a$ (R'=CH$_3$) described in Table II, there are prepared the esters of structure I$_a$ (R'=CH$_3$), described in Table III.

TABLE III

| RCO$_2$— | Formula | MP(°C.) |
|---|---|---|
| (CH$_3$)$_2$CHCH(CH$_3$)CO$_2$— | C$_{24}$H$_{36}$O$_5$ | 139–148 |
| 4-FC$_6$H$_4$CO$_2$— | C$_{26}$H$_{31}$FO$_5$ | 119.5–120.5 (vac) |
| (CH$_3$)$_2$CHCH$_2$CO$_2$— | C$_{24}$H$_{36}$O$_5$ | 126–128 |
| (CH$_3$)$_2$CHCO$_2$— | C$_{23}$H$_{34}$O$_5$ | 144–147 |
| CH$_3$(CH$_2$)$_3$CO$_2$— | C$_{24}$H$_{36}$O$_5$ | |
| CH$_3$CO$_2$— | C$_{21}$H$_{30}$O$_5$·0.1C$_4$H$_9$ | 153–156 (vac) |
| (adamantyl)CO$_2$— | C$_{30}$H$_{42}$O$_5$·0.05C$_6$H$_{12}$ | 155–158 |

CH$_3$(CH$_2$)$_6$CO$_2$—
C$_6$H$_{11}$CO$_2$—
CH$_2$=CH—CO$_2$—
CF$_3$(CH$_2$)$_2$CO$_2$—
C$_6$H$_5$CO$_2$—
4-ClC$_6$H$_4$CO$_2$—
2,4-F$_2$C$_6$H$_3$CO$_2$—
C$_6$H$_5$(CH$_2$)$_3$CO$_2$—
4-FC$_6$H$_4$CH$_2$CO$_2$—
2,4-F$_2$C$_6$H$_3$CH$_2$CO$_2$—
4-ClC$_6$H$_4$CH$_2$CO$_2$—
4-FC$_6$H$_4$(CH$_2$)$_3$CO$_2$—

CF$_3$
|
CH$_3$CH—CH$_2$CO$_2$—

(CH$_3$)$_2$C=CHCO$_2$— (cis)

CH$_2$=C(CH$_3$)CH$_2$CO$_2$—

CH$_3$(CH$_2$)$_8$CO$_2$—

(S)-CH$_3$CH$_2$CH(CH$_3$)CO$_2$— (with H and CH$_3$ stereochemistry shown)

EXAMPLE 2

6(R)-[2-(8'(S)-phenylacetoxy-2'(S),6'(R)-dimethyl-1',2',6',7',8',8'a(R)-hexahydronaphthyl-1'(S))ethyl]-4-(R)-hydroxy-3,4,5,6-tetrahydro-2H-pyran-2-one Step A: Preparation of 6(R)-[2-(8'(S)-phenylacetoxy-2'(S),6'(R)-dimethyl-1',2',6',7',8',8a'(R)-hexahydronaphthyl-1'(S))ethyl]-4(R)-dimethyl-tert-butylsilyloxy)-3,4,5,6-tetrahydro-2H-pyran-2-one, VI$_a$ (R'=CH$_3$)

A solution of 434 mg (1.0 mmol) of the alcohol V$_a$ (R'=CH$_3$) from Example 1, Step A, 204 mg (1.5 mmol) of phenylacetic acid, and 309 mg (1.5 mmol) of N,N'-dicyclohexylcarbodiimide in 10 ml of dichloromethane was treated with 22 mg (0.15 mmol) of 4-pyrrolidinopyridine and stirred at 20° under a nitrogen atmosphere. After 3 days the solvent was removed in vacuo and the residue was suspended in 25 ml of ether and filtered. Evaporation of the filtrate gave a viscous oil which has chromatographed on a 3×15 cm. column of silica gel (230–400 mesh). Elution (under air pressure) with ether-hexane (1:1,v:v) gave 460 mg (83%) of the title compound as a viscous oil: NMR (CDCl$_3$) δ0.10 (s,6,(CH$_3$)$_2$Si), 0.90 (s,9,(CH$_3$)$_3$CSi), 3.58 (s,2,PhCH$_2$—) 5.34 (m,1,naphthalene C$_8$H), 7.30 (s,5,Ph).

Employing the procedure of Example 2, Step A, but substituting for the phenylacetic acid used therein, an equimolecular amount of the organic acids of structure R—COOH described in Table IV there are produced the esters of structure VI$_a$ (R'=CH$_3$) also described in Table IV.

TABLE IV

| O<br>‖<br>R—C—O— | NMR(CDCl$_3$,δ) |
|---|---|
| cyclopropyl-CO$_2$— | 0.78–1.02 (m,4,cyclopropane) |
| CF$_3$<br>\|<br>CH$_3$CH—CH$_2$CO$_2$— | 1.04 (d,3,J=7 Hz,CH$_3$CHCF$_3$) |
| (CH$_3$)$_2$C=CHCO$_2$— | 1.88 (s,3,CH$_3$C=C)<br>2.17 (d,3,J=2 Hz,CH$_3$C=C)<br>5.68 (brs,1,C=CH—) |
| CH$_2$=C(CH$_3$)CH$_2$CO$_2$— | 1.80 (s,3,CH$_3$C=C)<br>4.86,4.92 (s,2,CH$_2$=C) |
| CH$_3$(CH$_2$)$_8$CO$_2$— | 0.87 (m,3,CH$_3$(CH$_2$)$_8$CO$_2$—)<br>1.25 (m,14,CH$_3$(CH$_2$)$_7$CH$_2$CO$_2$—) |
| (S)-CH$_3$CH$_2$CH(CH$_3$)CO$_2$— | |
| 4-FC$_6$H$_4$CO$_2$— | |
| CH$_3$CO$_2$— | |
| CH$_3$CH$_2$CH(CH$_3$)CO$_2$— | |

TABLE IV-continued

| R—C(=O)—O— | NMR(CDCl$_3$,δ) |
|---|---|

(CH$_3$)$_2$CHCH$_2$CO$_2$—
(CH$_3$)$_2$CHCO$_2$—
CH$_3$(CH$_2$)$_3$CO$_2$—

[structure: cyclopropyl-type with C—CO$_2$—]

[structure: cyclopropyl-type with C—CO$_2$—]

[structure: vinyl-C—CO$_2$—]

[structure: —C—CO$_2$—]

CH$_3$(CH$_2$)$_6$CO$_2$—
C$_6$H$_{11}$CO$_2$—
CH$_2$=CH—CO$_2$—
CF$_3$(CH$_2$)$_2$CO$_2$—
C$_6$H$_5$CO$_2$—
4-ClC$_6$H$_4$CO$_2$—
2,4-F$_2$C$_6$H$_3$CO$_2$—
C$_6$H$_5$(CH$_2$)$_3$CO$_2$—
4-FC$_6$H$_4$CH$_2$CO$_2$—
2,4-F$_2$C$_6$H$_3$CH$_2$CO$_2$—
4-ClC$_6$H$_4$CH$_2$CO$_2$—
4-FC$_6$H$_4$(CH$_2$)$_3$CO$_2$—

Step B: Preparation of 6(R)-[2-(8'(S)-phenylacetoxy-2'(S),6'(R)-dimethyl-1',2',6',7',8',8'a(R)-hexahydronaphthyl-1'(S))ethyl]-4(R)-hydroxy-3,4,5,6-tetrahydro-2H-pyran-2-one, I$_a$ (R'=CH$_3$)

Employing the procedure substantially as described in Example 1, Step C, but substituting for the propanoyloxy compound used therein an equimolar amount of the phenylacetoxy compound from Example 2, Step A, there is produced the title compound, m.p. 109°–112° C.

Employing the other esters, VI$_a$ (R'=CH$_3$) described in Example 2, Step A, (Table IV) and following the procedure of Example 2, Step B, there are produced the esters of structure I$_a$ (R'=CH$_3$) described in Table V.

TABLE V

| RCO$_2$ | Formula | m.p. (°C.) |
|---|---|---|
| [cyclopropyl]—CO$_2$ | C$_{23}$H$_{32}$O$_5$ | 116–119 |
| CH$_3$CH(CF$_3$)CH$_2$CO$_2$ | C$_{24}$H$_{33}$F$_3$O$_5$ | 110–113 |
| (CH$_3$)$_2$C=CH—CO$_2$— | C$_{24}$H$_{34}$O$_5$ | 113–118 |
| CH$_2$=C(CH$_3$)CH$_2$CO$_2$— | C$_{24}$H$_{34}$O$_5$ | 116–119 |
| CH$_3$(CH$_2$)$_8$CO$_2$— | C$_{29}$H$_{46}$O$_5$ | (wax) |
| CH$_3$CH(CH$_3$)CH(H)CO$_2$— (chiral) | C$_{24}$H$_{36}$O$_5$ | 126–129 |
| 4-F-C$_6$H$_4$—CO$_2$— | | |
| CH$_3$CH$_2$CH(CH$_3$)C(=O)O— | | |

(CH$_3$)$_2$CHCH$_2$CO$_2$—
(CH$_3$)$_2$CHCO$_2$—
CH$_3$(CH$_2$)$_3$CO$_2$—

[structure: C—CO$_2$—]

[structure: C—CO$_2$—]

[structure: vinyl-C—CO$_2$—]

[structure: —C—CO$_2$—]

CH$_3$(CH$_2$)$_6$CO$_2$—
C$_6$H$_{11}$CO$_2$—
CH$_2$=CH—CO$_2$—
CF$_3$(CH$_2$)$_2$CO$_2$—
C$_6$H$_5$CO$_2$—
4-ClC$_6$H$_4$CO$_2$—
2,4-F$_2$C$_6$H$_3$CO$_2$—
C$_6$H$_5$(CH$_2$)$_3$CO$_2$—
4-FC$_6$H$_4$CH$_2$CO$_2$—
2,4-F$_2$C$_6$H$_3$CH$_2$CO$_2$—
4-ClC$_6$H$_4$CH$_2$CO$_2$—
4-FC$_6$H$_4$(CH$_2$)$_3$CO$_2$—

EXAMPLE 3

6(R)-[2-(8'(S)-2''-ethyl-2''-methylbutyryloxy-2'(S)-6'(R)-dimethyl-1',2',6',7',8',8'a(R)-hexahydronaphthyl-1'(S))ethyl]-4(R)-hydroxy-3,4,5,6-tetrahydro-2H-pyran-2-one

Step A: Preparation of 6(R)-[2-(8'(S)-2''-ethyl-2''-methylbutyryloxy-2'(S)-6'(R)-dimethyl-1',2',6',7',8',8'a(R)-hexahydronaphthyl-1'(S))-ethyl]-4(R)-(dimethyl-tert-butylsilyloxy)-3,4,5,6-tetrahydro-2H-pyran-2-one VI$_a$ (R'=CH$_3$)

3.0 g of 2-ethyl-2-methylbutyryl chloride (20 mmol) was added to a magnetically stirred solution of 2.17 g (5 mmol) of alcohol V$_a$ (R'=CH$_3$) and 74 mg of 4-pyrrolidinopyridine in 20 ml of pyridine. This reaction mixture was stirred at 100° C. under an atmosphere of N$_2$ for nine hours. The reaction mixture was diluted with 500 ml ether and washed with 1 N HCl until the wash was acidic and then with brine (3×50 ml). After drying over MgSO$_4$, the solution was filtered and evaporated to give 4.2 g of a brown oil. This oil was chromatographed on a 6×15 cm column of silica gel (230–400 mesh). Elution (under air pressure) with ether-hexane (1:1, v:v) gave 2.6 g (95%) of the title compound as a viscous yellow oil: NMR (CDCl$_3$) δ.0.08 (s,6, (CH$_3$)$_2$Si), 0.9(s,9,(CH$_3$)$_3$ CSi), 2.57 (d,2,J=4 Hz, pyran C$_3$H's), 4.30 (m, 1 pyran, C$_4$H), 4.63(m,1,pyran C$_6$H), 5.42(m,1,naphthalene C$_8$H), 5.53(m,1,naphthalene C$_5$H), 5.78(dd,1,J=6,Hz, 10 Hz, naphthalene C$_3$H), 6.03(d,1,J=10 Hz, naphthalene C$_4$H).

Employing the procedure substantially as described in Example 3, Step A, but substituting for the 2-ethyl-2-methylbutyryl chloride used therein, an equimolecular amount of the acid chlorides of structure R—COCl, described in Table VI, there are produced the esters of structure VI$_a$ (R'=CH$_3$) also described in Table VI.

TABLE VI

| $\underset{R-CO}{\overset{O}{\parallel}}$ | NMR(CDCl$_3$,δ) |
|---|---|
|  | 0.87 (m,9,CH$_3$CH$_2$CH$_2$(CH$_3$CH$_2$)$_2$CCO$_2$) |
| 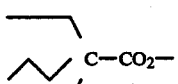 | 0.78 (t,9,J=Hz,(CH$_3$CH$_2$)$_3$CCO$_2$) <br> 1.48 (q,6,J=7 Hz,(CH$_3$CH$_2$)$_3$CCO$_2$) |
| 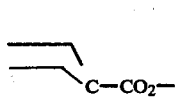 | 1.28 (s,6,(CH$_3$)$_2$CCO$_2$) <br> 2.20 (s,3,CH$_3$—C=CH$_2$) <br> 3.86 (m,2,CH$_2$=C) |
| 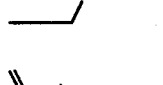 | 1.12 (s,6,(CH$_3$)$_2$CCO$_2$) <br> 0.83 (t,3,CH$_3$—CH$_2$CCO$_2$) |

Step B: Preparation of 6(R)-[2-(8'(S)-2''-ethyl-2''-methylbutyryloxy-2'(S)-6'(R)-dimethyl-1',2',6',7',8',8'a(R)-hexahydronaphthyl-1'(S))ethyl]-4(R)-hydroxy-3,4,5,6-tetrahydro-2H-pyran-2-one Employing the procedure substantially as described in Example 1, Step C, or Example 2, Step B, but employing as starting material the silyl ether compound from Example 3, Step A, there is produced the title compound, m.p. 111°–113° C. (C$_{26}$H$_{40}$O$_5$).

Similarly prepared are the esters of structure I$_a$ described in Table VII, employing as starting materials the other esters VI$_a$ (R'=CH$_3$) described in Table VI.

TABLE VII

| RCO$_2$— | Formula | m.p. (°C.) |
|---|---|---|
| 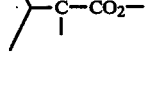 | C$_{28}$H$_{44}$O$_5$ | 81–83 |
| 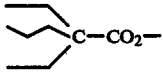 | C$_{27}$H$_{42}$O$_5$ | 129–132 |
| 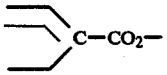 | C$_{26}$H$_{38}$O$_5$ | 75–78 |
| 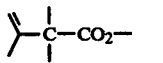 | C$_{25}$H$_{38}$O$_5$ | 135–138 |

Employing the procedures of Example 1, Step A, followed by Example 1, Steps B and C, or Example 2 or 3, Steps A and B, but substituting for the diol of structure IV$_a$ (R'=CH$_3$) in Example 1, Step A, the corresponding diols of structure IV$_a$ (R'=H) or IV$_{b,c,d}$, or $_e$ (R'=H, or CH$_3$), there are produced in sequence the silyl ethers of structures V$_a$ (R'=H) or V$_{b,c,d}$, and $_e$ (R'=H or CH$_3$), the esters of structure VI$_a$ (R'=H) or VI$_{b,c,d}$, and $_e$ (R'=H, or CH$_3$), and the novel esters of structures I$_a$ (R'=H) or I$_{b,c,d}$ and $_e$ (R'=H or CH$_3$) in accordance with Flow Sheet A, wherein $$\underset{R-CO}{\overset{O}{\parallel}}$$

of the 8'-alkanoyl group is:

| | |
|---|---|
| 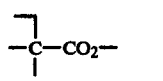 | 4-ClC$_6$H$_4$CO$_2$— |
| CH$_3$CO$_2$— | 2,4-F$_2$C$_6$H$_3$CO$_2$— |
| | C$_6$H$_5$(CH$_2$)$_3$CO$_2$— |
| 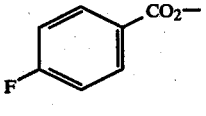 | |
| (CH$_3$)$_2$CHCH$_2$CO$_2$— | 4-FC$_6$H$_4$CH$_2$CO$_2$— |
| (CH$_3$)$_2$CHCO$_2$ | 2,4-F$_2$C$_6$H$_3$CH$_2$CO$_2$— |
| CH$_3$(CH$_2$)$_3$CO$_2$— | 4-ClC$_6$H$_4$CH$_2$CO$_2$— |

-continued

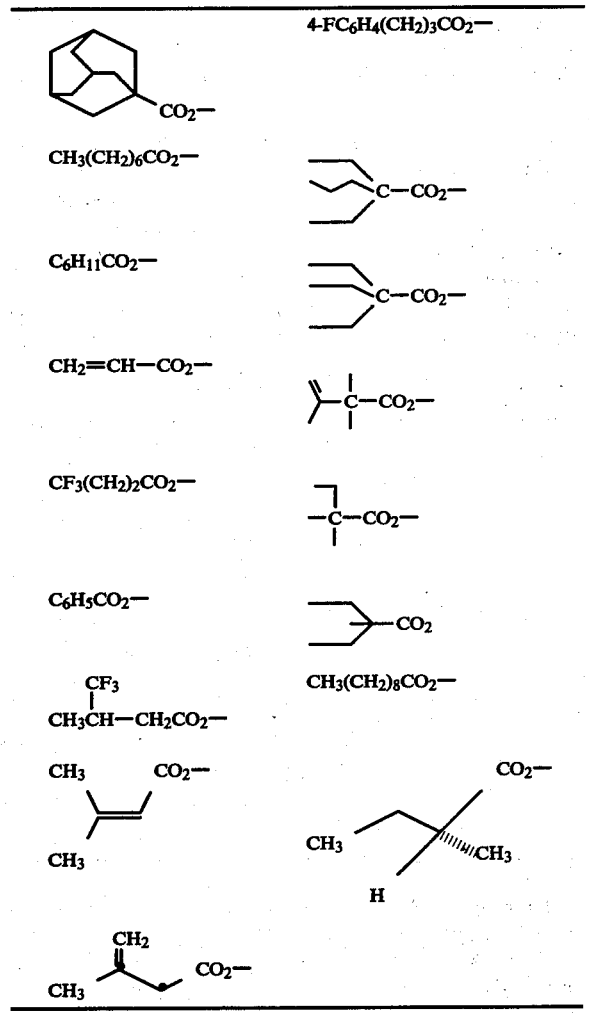

EXAMPLE 4

Preparation of
6(R)-{2-[8(S)(2"-ethyl-2"-methylbutyryloxy)-2'(S),6'(S)-dimethyl-1',2',3',4',4'a(S),5',6',7',8',8'a(S)-decahydronaphthyl-1'(S)]ethyl}-4(R)hydroxy-3,4,5,6-tetrahydro-2H-pyran-2-one, $I_e$ (R'=CH$_3$)

Step A: Preparation of 6(R)-[2-(8'(S)hydroxy-2'(S),6'(S)dimethyl-1',2',3',4',4'a(S),5',6',7',8',8'a(S)-decahydronaphthyl-1'(S))ethyl]-4(R)-hydroxy-3,4,5,6-tetrahydro-2H-pyran-2-one IV$_e$ (R'=CH$_3$)

A solution of 2.0 g (6.2 mmol) of the alcohol IV$_a$ (R'=CH$_3$) in 100 ml of ethyl acetate was hydrogenated in the presence of platinum oxide (1 g) at 40 lbs. pressure until an uptake of two mole equivalents of hydrogen was observed. The catalyst was removed by filtration and the filtrate was evaporated to dryness to provide a white solid (1.9 g) which was chromatographed on a 6×20 cm column of silica gel (230-400 mesh). Elution (under air pressure) with acetone-methylene chloride (3:7, v:v) gave 1.0 g (50%) of the title compound as a colorless solid.

An analytical sample was prepared by recrystallization of a portion of the material from chloroform to give a white cottony solid: m.p. 166°-8°.

Step B: Preparation of 6(R)-[2-(8'(S)-hydroxy-2'(S),6'(S)-dimethyl-1',2',3',4',4'a(S),5',6',7',8',8'a(S)-decahydronaphthyl-1'(S)-ethyl]4(R)-(dimethyl-tert-butylsilyloxy)-3,4,5,6-tetrahydro-2H-pyran-2-one, V$_e$ (R'=CH$_3$)

A solution of the alcohol IV$_e$ (R'=CH$_3$) (1.0 g, 3.1 mmol), imidazole (1.05 g, 15.4 mmol) and tert-butyldimethylchlorosilane (1.16 g, 7.7 mmol) in 20 ml of N,N-dimethyl formamide was stirred at 20° under a nitrogen atmosphere for 18 hours. The reaction solution was diluted with 200 ml of ether and washed successively with water, 2% aqueous hydrochloric acid and brine. The ether solution was dried over MgSO$_4$ and evaporated to provide a white solid (1.8 g) which was chromatographed on a 6×20 cm column of silica (230-400 mesh). Elution under air pressure with acetone:methylene chloride (1:19, v:v) gave 1.0 g (74%) of the title compound as a white solid: m.p. 136°-138° C.

Step C: Preparation of 6(R)-{2-[8'(S)(2"-ethyl-2"-methylbutyryloxy)-2'(-S),6'(S)-dimethyl-1',2',3',4',4'a(S),5',6',7',8',8'a(S)-decahydronaphthyl-1'(S)]ethyl]}-4(R)(dimethyl-tert-butylsilyloxy)-3,4,5,6-tetrahydro-2H-pyran-2-one VI$_e$ (R'=CH$_3$)

By substituting an equimolar amount of alcohol V$_e$ (R'=CH$_3$) for alcohol V$_a$ (R'=CH$_3$) in Step A of Example 3 and following the procedure for Step A there was obtained a corresponding amount of the title compound, VI$_e$ (R'=CH$_3$) as a yellow oil. NMR(CDCl$_3$) δ 0.08(S,6,(CH$_3$)$_2$Si), 0.90 (S,9,(CH$_3$)$_3$)CSi), 1.13 (S,6,(CH$_3$)$_2$CO$_2$), 2.63(m,2,pyran C$_3$H's), 4.33 (m,1,pyran C$_4$H), 4.60 (m,1,pyran C$_6$H), 5.23 (m,1,naphthylene C$_8$H).

Step D: Preparation of 6(R)-{2-[8'(S)(2"-ethyl-2"-methylbutyryloxy)-2'(S),6(S)-dimethyl-1',2',3',4',4'a(S),5',6',7',8',8'a(S)-decahydronaphthyl-1'(S)ethyl}-4(R)-hydroxy-3,4,5,6-tetrahydro-2H-pyran-2-one, I$_e$ (R'=CH$_3$)

By substituting an equimolar amount of the silyl ether VI$_e$ (R'=CH$_3$) from Example 4, Step C for the silyl ether in Step C of Example 1 and following the procedure for Step C of Example 1 there was obtained a corresponding amount of the title compound as a solid.

An analytical sample was prepared by recrystallization of the material from hexane to obtain white needles: m.p. 146°-147° C.

Employing the procedure substantially as described in Example 4 Steps A through D, but substituting for the diol of structure IV$_a$ (R'=CH$_3$) in Step A, an equimolecular amount of the diol of structure IV$_a$ (R'=H) there are produced in sequence the compounds: IV$_e$ (R'=H) in Step A; V$_e$(R'=H) in Step B; VI$_e$(R'=H) in Step C; and I$_e$ (R'=H) in Step D.

EXAMPLE 5

6(R)-{2-[8'(S)-(2''-ethyl-2''-methylbutyryloxy)-2'(S),6'(R)-dimethyl-1',2',3',4',6',7',8'a(S)-octahydronaphthyl-1'(S)]ethyl}-4(R)-hydroxy-3,4,5,6-tetrahydro-2H-pyran-2-one, $I_b$ (R'=CH$_3$)

Step A: Preparation of 6(R)-[2-(8'(S)-hydroxy-2'(S),6'(R)-dimethyl-1',2',3',4',6',7',8'a(S)-octahydronaphthyl-1'(S)-ethyl]-4(R)hydroxy-3,4,5,6-tetrahydro-2H-pyran-2-one, $IV_b$ (R'=CH$_3$)

Employing the procedure substantially as described for the preparation of the starting material $IV_a$ (R'=CH$_3$) by hydrolysis of MK-803 with refluxing aqueous LiOH.H$_2$O for 56 hours but substituting for the MK-803 an equimolecular amount of compound $III_b$ (R'=CH$_3$) there is produced, in comparable yield, the title compound $IV_b$ (R'=CH$_3$), m.p. 136°-139° C.

Following the procedure of Example 4, Steps B, C, and D, but substituting for the compound $IV_e$ (R'=CH$_3$) used in Step B thereof, an equimolecular amount of compound $IV_b$ (R'=CH$_3$) from Step A of this example, there is produced in comparable yields to those experienced in Example 4, the following compounds:

Step B:
6(R)-[2-(8'(S)-hydroxy-2'(S),6'(R)-dimethyl-1',2',3',4',6',7',8'a(S)-octahydronaphthyl-1'(S)-ethyl]-4(R)-(dimethyl-tert-butylsilyloxy)-3,4,5,6-tetrahydro-2H-pyran-2-one, $V_b$ (R'=CH$_3$), m.p. 140°-142° C.

Step C:
6(R)-{2-[(8'(S)-(2''-ethyl-2''-methylbutyryloxy)-2'(S),6'(R)-dimethyl-1',2',3',4',6',7',8'a(S)-octahydronaphthyl-1'(S)]ethyl}-4(R)-(dimethyl-tert-butylsilyoxy)-3,4,5,6-tetrahydro-2H-pyran-2-one, $VI_{(b)}$ (R'=CH$_3$) wherein

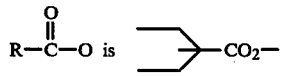

Step D:
6(R)-2-[8'-(S)(2''-ethyl-2''-methylbutyryloxy)-2'(S),6'(R)-dimethyl-1',2',3',4',6',7',8'a(S)-octahydronaphthyl-1'(S)]ethyl-4(R)-hydroxy-3,4,5,6-tetrahydro-2H-pyran-2-one, $I_b$(R'=CH$_3$) m.p. 129°-131° C. wherein

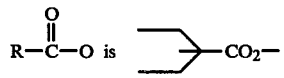

Following the procedure substantially as described in Example 5, but using $III_b$ (R'=H) or $III_c$, $III_d$, or $III_e$ (R'=H or CH$_3$) as starting material in place of $III_b$ (R'=CH$_3$) there are produced in turn compounds $IV_b$ (R'=H) or $IV_{c,d,e}$ (R'=H or CH$_3$), $V_b$ (R'=H) or $V_{c,d,e}$ (R'=H or CH$_3$), $VI_b$ (R'=H) or $VI_{c,d,e}$ (R'=H or CH$_3$) and $I_b$ (R'=H) or $I_{c,d,e}$ (R'=H or CH$_3$) wherein

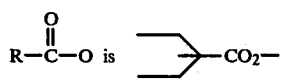

EXAMPLE 6

Step 1: Preparation of 6(R)-[2-(8'(S)-Hydroxy-2'(S),6'(R)-dimethyl-1',2',6',7',8',8'a(R)-hexahydronaphthyl-1'(S))ethyl]-4(R)-hydroxy-3,4,5,6-tetrahydro-2H-pyran-2-one A mixture of mevinolin (50.2 g, 0.124 mole) and LiOH.H$_2$O (52.0 g, 1.24 mole) in water (3 L) was magnetically stirred at reflux under a N$_2$ atmosphere for 72 hours. The stirred mixture was cooled to 0° C. (ice/acetone bath) and treated with 12 N HCl (120 ml, 1.44 mole) at such a rate that the temperature did not exceed 3° C. This mixture was saturated with solid NaCl and extracted with ether (4×500 ml). The combined extracts were washed with brine (2×250 ml), dried over MgSO$_4$ and evaporated to give an orange oil (31.7 g). This oil was dissolved in toluene (250 ml) and the solution was refluxed under a N$_2$ atmosphere for 4 hours with continuous separation of the water in a Dean-Stark apparatus to effect relactonization. Evaporation of the toluene left an oily residue which was dissolved in ether (1.5 L). This solution was washed with saturated NaHCO$_3$ (250 ml), H$_2$O (250 ml) and brine (250 ml), dried and evaporated to provide a solid residue. Trituration of this solid with hexane (200 ml) gave the title compound as a cream colored solid (29.7 g, 75%) which did not require further purification for synthetic purposes. An analytical sample was prepared by recrystallizing a portion of the above solid from n-butyl chloride to provide colorless clusters, mp 128°-131° C.

Step 2: Preparation of 6(R)-[2-(8'(S)-Hydroxy-2'(S),6'(R)-dimethyl-1',2',6',7',8',8'a(R)-hexahydronaphthyl-1'(S))ethyl]-4(R)-tert-butyldimethylsilyloxy-3,4,5,6-tetrahydro-2H-pyran-2-one A solution of the alcohol (18.3 g, 0.057 mole), tert-butyldimethylsilylchloride (10.3 g, 0.068 mole) and imidazole (9.3 g, 0.137 mole) in DMF (200 ml) was magnetically stirred at ambient temperature for 18 hours. The reaction mixture was diluted with ether (1500 ml) and washed successively with water (200 ml), 2% aqueous HCl (200 ml), water (200 ml), saturated NaHCO$_3$ (200 ml) and water (2×200 ml) and dried over MgSO$_4$. The filtered ether solution was concentrated to one liter, diluted with 600 ml hexane and the resultant solution concentrated to 600 ml to provide a white solid (13.7 g). A second crop of crystals (3.4 g) was obtained by reducing the mother liquor to 250 ml and storing at 0° C. overnight. The combined yield was 17.1 g (69%) and the solid melted at 142°-4° C.

Step 3: Preparation of 6(R)-[2-(8'(S)-Hydroxy-2(S),6(S)-dimethyl-1,2,3,4,4a(S),-5,6,7,8,8a(S)-decahydronaphthyl-1'(S))ethyl]-4(R)-tert-butyldimethylsilyloxy-3,4,5,6-tetrahydro-2H-pyran-2-one A mixture of the silyl ether (5.0 g, 0.0115 mole), and PtO$_2$ (1.0 g) in ethylacetate (200 ml) was hydrogenated in the Paar low pressure hydrogenator overnight. The catalyst was removed by filtration and the filtrate was concentrated to dryness leaving a white solid. This solid was chromatographed on a 80 mm column containing 7" of silica gel (230-400 mesh). Elution under air pressure with methylene chloride/acetone (98:2, v:v, 1.5 L) provided a forerun which was discarded. Continued elution with the same eluant (2 L) gave the title compound as a white solid (3.4 g, 67%), mp 146°-7° C.

Step 4: Preparation of
6(R)-[2-[8'(S)-(2,2-Dimethylbutyryloxy)-2'(S),6'(S)-dimethyl-1',2',3',4',4'a(S),5',6',7',8',8'a(S)-decahydronaphthyl-1'(S)]ethyl]-4(R)-tert-butyldimethylsilyloxy-3,4,5,6-tetrahydro-2H-pyran-2-one The 2,2-dimethylbutyryl chloride (0.067 g, 0.0005 mole) was added to a magnetically stirred solution of the alcohol (0.11 g, 0.00025 mole) and 4-pyrrolidinopyridine (0.0074 g, 0.00005 mole) in pyridine (2 ml). After heating this solution at 100° C. for 3 hours under $N_2$, another 0.0335 g of 2,2-dimethylbutyryl chloride and 0.0039 g of 4-pyrrolidinopyridine was added and heating was continued for another 3 hours.

The reaction was cooled, diluted with ether (50 ml), and washed with 3 N HCl (2×5 ml) and brine (2×10 ml). The ether solution was dried over $MgSO_4$, filtered and evaporated to provide a yellow oil (0.136 g). This oil was chromatographed on a 30 mm column containing 6" of silica gel (230-400 mesh). The column was eluted under air pressure with $CH_2Cl_2$ (300 ml) and then $CH_2Cl_2$/acetone (98:2, v:v, 100 ml) to provide a forerun which was discarded. Continued elution with $CH_2Cl_2$/acetone (98:2, v:v, 50 ml) gave the desired product as a pale yellow oil (0.081 g, 60%).

Step 5: Preparation of
6(R)-[2-[8'(S)-(2,2-Dimethylbutyryloxy)-2'(S)-6'(S)-dimethyl-1',2',3',4',4'a(S),5',6',7',8',8'a(S)-decahydronaphthyl-1'(S)]ethyl]4(R)-hydroxy-3,4,5,6-tetrahydro-2H-pyran-2-one The silyl ether (0.5 g, 0.00093 mole) was added to a THF (30 ml) solution containing glacial HOAc (0.224 g, 0.00372 mole) and tetrabutylammonium fluoride trihydrate (0.88 g, 0.00279 mole). This solution was stirred magnetically under a $N_2$ atmosphere for 48 hours. The reaction solution was diluted with ether (150 ml) and washed with $H_2O$ (25 ml) and brine (2×75 ml). The ether solution ws dried over $MgSO_4$, filtered and evaporated to give a viscous oil (0.45 g). This oil was chromatographed on a 40 mm column containing 6" of silica gel (230-400 mesh). The column was eluted with $CH_2Cl_2$/acetone (85:15, v:v) under air pressure and 20 ml fractions were collected. Fractions 21-37 were combined and concentrated to dryness to provide the title compound as a solid (0.37 g, 94%). An analytical sample was prepared by recrystallizing the solid from ether/hexane to give colorless plates, mp 159°-160° C.

Employing the procedure substantially as described in Example 6, Steps 1, 2, 4 and 5, but substituting for the mevinolin used in Step 1 thereof an equimolecular amount of each of the starting materials described in Table VIII there are produced the respective 2,2-dimethylbutyryloxy compounds, also described in Table VIII in accordance with the following reaction scheme:

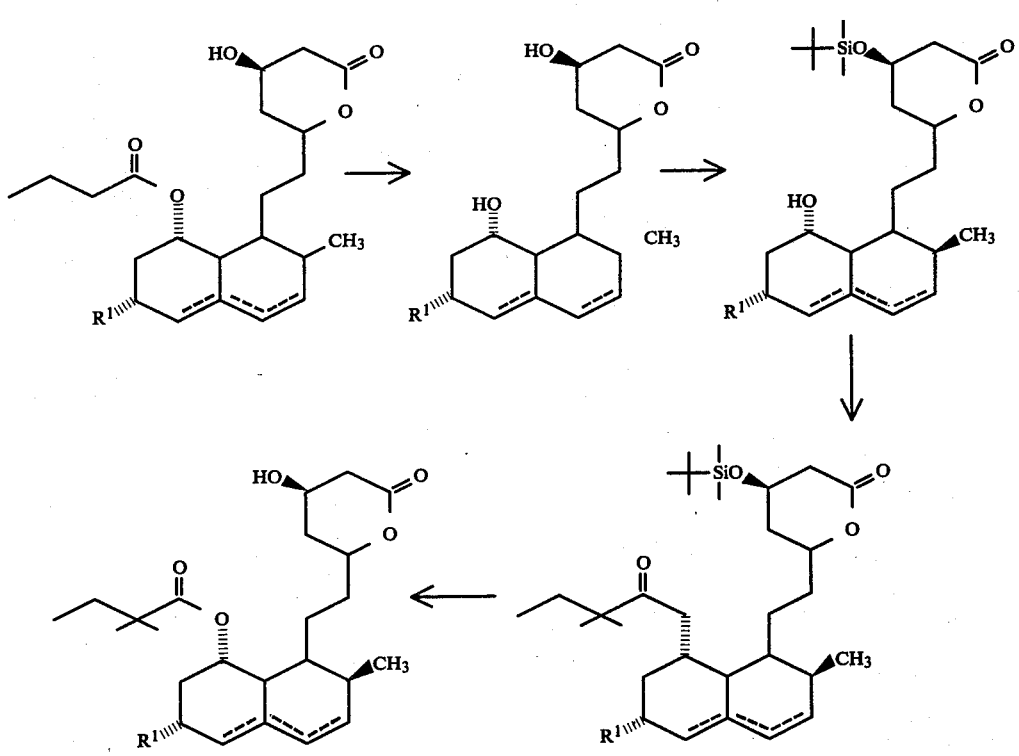

TABLE VIII

| R' | X | Y | Z | m.p. product |
|---|---|---|---|---|
| H | double | single | double | 75-79° C. |
| H | single | single | single | 130-131° C. |
| —$CH_3$ | single | single | double | 158-159° C. |
| —$CH_3$ | single | double | single | 75-77° C. |
| —$CH_3$ | double | single | single | 128-129° C. |

EXAMPLE 7

Ethyl 3(R),5(R)-dihydroxy-7-[8(S)-(2,2-dimethylbutyryloxy)-2(S),6(S)-dimethyl-1,2,3,4,4a(S),5,6,7,8,8a(S)-decahydronaphthyl-1(S)]heptanoate Sodium methoxide (30 mg) is added to a stirred suspension of the lactone from Example 6 (3.0 g) in ethanol (50 ml) under a nitrogen atmosphere. The resultant solution is stirred at ambient temperature for ½ hour and then diluted with ether (300 ml). The ethereal solution is washed with H₂O (3×50 ml), dried over MgSO₄ and filtered. The filtrate is evaporated in vacuo leaving an oil which is chromatographed on a 60 mm column containing 6" of silica gel (230–400 mesh). Elution with methylene chloride/ethanol (96:4, V:V, 250 ml) under air pressure gives the title compound as a solid.

EXAMPLE 8

2,3-Dihydroxypropyl 3(R),5(R)-dihydroxy-7-[8(S)-(2,2-dimethylbutyryloxy)-2(S),6(S)-dimethyl-1,2,3,4,4a(S),5,6,7,8,8a(S)-decahydronaphthyl-1(S)]heptanoate The sodium salt of the dihydroxy acid of the compound from Example 6 is prepared by adding 1 N NaOH (0.55 ml) to a solution of the lactone, 0.22 g in DMF (2 ml). After stirring this solution for 15 minutes, 1-iodo-2,3-dihydroxypropane (0.2 g) is added and the stirred solution is heated at 80° C. (oil bath) for 6 hours. After cooling to ambient temperature, the reaction solution is poured into ether (100 ml). This ethereal solution is washed with brine (2. .25 ml), dried over MgSO₄ and filtered. The filtrate is evaporated in vacuo leaving an oil which is chromatographed on a 20 mm column containing 6" of silica gel (230–400 mesh). Elution with acetone-methylene chloride (60:40; v:v;) under air pressure provides the title compound as an oil which solidifies upon storing in the freezer overnight.

EXAMPLE 9

Typical formulations for filling a size 0 hard gelatin capsule comprising 3.125, 6.25, 12.5, 25 or 50 mg of one of the novel compounds of this invention such as the products of Example 3, Step B, Example 1, Step C, or Example 6, Step 5 and sufficient finely divided lactose to provide a total capsule content of about 580–590 mg.

What is claimed is:

1. A compound of the formula:

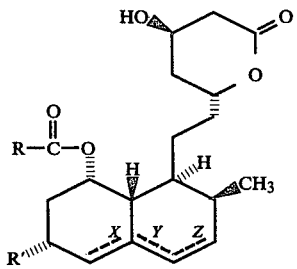

wherein
R' is H or CH₃;
R is 1-ethyl-1-methylpropyl, 1,1-diethylpropyl, 1,1-dimethyethyl, or 1,1-diethylbutyl,
the dotted lines at X, Y and Z represent possible double bonds, said double bonds, when any are present, being either X and Z in combination or X, Y or Z alone; or
the corresponding dihydroxy acid of the formula:

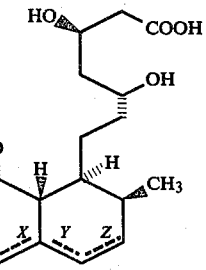

or a pharmaceutically acceptable salt of said acid, a C₁₋₄alkyl ester of said acid, a phenyl- dimethylamino-, or acetylamino-substituted-C₁₋₄ alkyl ester or α-monoglyceride of said acid.

2. The compound of claim 1 wherein R' is CH₃.

3. The compound of claims 1 or 2, wherein none of X, Y or Z is a double bond.

4. A pharmaceutical antihypercholesterolemic composition comprising a pharmaceutical carrier and an antihypercholesterolemic effective amount of a compound of structural formula:

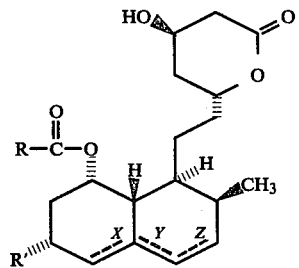

in which
R' is H, or CH₃;
R is 1-ethyl-1-methylpropyl, 1,1-diethylpropyl, 1,1-dimethyethyl, or 1,1-diethylbutyl,
the dotted lines at X, Y and Z represent possible double bonds, said double bonds, when any are present, being either X and Z in combination or X, Y or Z alone; or
the corresponding dihydroxy acid of the formula:

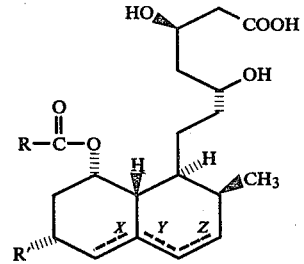

or a pharmaceutically acceptable salt of said acid, a C₁₋₄alkyl ester of said acid, a phenyl- dimethylamino-, or acetylamino-substituted-C₁₋₄ alkyl ester or α-monoglyceride of said acid.

5. The composition of claim 4 wherein R' is CH₃.

6. The composition of claim 4 or 5, wherein none of X, Y or Z is a double bond.

7. A method of treating hypercholesterolemia in a patient in need of such treatment which comprises administration of an antihyperchloesterolemic effective amount of a compound of structural formula:

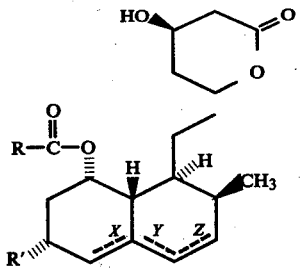

wherein
R' is H or CH$_3$;
R is 1-ethyl-1-methylpropyl, 1,1-diethylpropyl, 1,1-dimethyethyl, or 1,1-diethylbutyl,
the dotted lines at X, Y and Z represent possible double bonds, said double bonds, when any are present, being either X and Z in combination or X, Y or Z alone; or the corresponding dihydroxy acid of the formula:

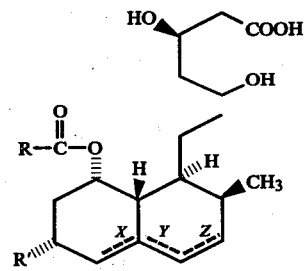

or a pharmaceutically acceptable salt of said acid, a C$_{1-4}$alkyl ester of said acid, a phenyl- dimethylamino-, or acetylamino-substituted-C$_{1-4}$ alkyl ester or α-monoglyceride of said acid.

8. The method of claim 7 wherein R' is CH$_3$.

9. The method of claim 7 or 8, wherein none of X, Y or Z is a double bond.

* * * * *